United States Patent [19]

Honjo et al.

[11] Patent Number: 5,530,098
[45] Date of Patent: Jun. 25, 1996

[54] HUMAN B-CELL DIFFERENTIATION FACTOR AND PROCESS OF PRODUCING SAID FACTOR

[75] Inventors: Tasuku Honjo, Osaka; Kiyoshi Takatsu, Kumamoto-ken, both of Japan; Eva Severinson, Stockholm, Sweden

[73] Assignee: Suntory Limited, Osaka, Japan

[21] Appl. No.: 257,525

[22] Filed: Jun. 8, 1994

Related U.S. Application Data

[62] Division of Ser. No. 99,467, Sep. 21, 1987, Pat. No. 5,324,640.

[30] Foreign Application Priority Data

Sep. 20, 1986 [JP] Japan .................. 61-223284

[51] Int. Cl.$^6$ .................. C07K 14/715; C12P 21/02; C12N 15/24
[52] U.S. Cl. .................. 530/351; 424/85.1; 424/85.2; 530/413; 530/416; 530/417; 435/69.52
[58] Field of Search .................. 530/351, 413, 530/416, 417; 424/85.2, 85.1; 435/69.52

[56] References Cited

U.S. PATENT DOCUMENTS

| | | | |
|---|---|---|---|
| 5,310,550 | 5/1994 | Kishimoto et al. | 424/85.2 |
| 5,324,640 | 6/1994 | Honjo et al. | 435/69.52 |
| 5,362,489 | 11/1994 | Kishimoto et al. | 424/852 |

FOREIGN PATENT DOCUMENTS

8704466  7/1987  WIPO.

OTHER PUBLICATIONS

Azuma et al. (1986) *Nucleic Acids Research* 14:9149–9158.

Hirano et al. (1985) *Proc. Natl. Acad. Sci. USA* 82:5490–5494.

Takatsu et al. (1985) *J. Immunol.* 134:382–389.

Nucleic Acids Research, vol. 14, No. 22, Nov. 22, 1988, pp. 9149–9158, Azuma: "Cloning of cDNA for human T–cell replacing factor (interluekin–5) and comparison with the murine homologue".

Proc. Natl. Acad. Sci. USA, vol. 84, Jun. 1987, pp. 4234–4238, Takatsu: "Interleukin 5 . . . ".

Chemical Abstracts, vol. 106, No. 21, May 1987, p. 152, No. 169856b, Kinashi: "Clowning of cDNA to T–cell replacing factor and identity with B–cell growth factor II".

Tsujimoto et al. "Purification and Charcterization of Recombinant Human Interleukin 5 Expressed in Chinese Hamster Ovary Cells". J. Biochem., 106, pp. 23–28 (1989).

Primary Examiner—Garnette D. Draper
Assistant Examiner—Prema Mertz
Attorney, Agent, or Firm—Cushman, Darby & Cushman

[57] ABSTRACT

A cDNA and a chromosomal DNA coding for the human B-cell differentiation factor were provided and the entire nucleotide sequence of said DNAs as well as the entire amino acid sequences of the polypeptide portion of mature human B-cell differentiation factor and the leader peptide were revealed. The method for producing human B-cell differentiation factor by a recombinant gene technology was also provided.

6 Claims, 14 Drawing Sheets

Fig. 1

```
ATGCACTTTCTTGCCAAAGGCAAACGCAGAACGTTTCAGAGCC

ATG AGG ATG CTT CTG CAT TTG AGT TTG CTA GCT CTT GGA GCT GCC
TAC GTG TAT GCC ATC CCC ACA GAA ATT CCC ACA AGT GCA TTG GTG
AAA GAG ACC TTG GCA CTG CTT TCT CAT CGA ACT CTG CTG ATA
GCC AAT GAG ACT CTG AGG ATT CCT GTT CCT GTA CAT AAA AAT CAC
CAA CTG TGC ACT GAA GAA ATC TTT CAG GGA ATA GGC ACA CTG GAG
AGT CAA ACT GTG CAA GGG GGT ACT GTG GAA AGA CTA TTG AAA AAC
TTG TCC TTA ATA AAG AAA TAC ATT GAC GGC CAA AAA AAA AAG TGT
GGA GAA AGA CGG AGA GTA ATG AAC CAA TTC CTA GAC TAC CTG CAA
GAG TTT CTT GGT GTA ATG AAC ACC GAG TGG ATA ATA GAA AGT TGA
GACTAAACTGGTTTGTTGCAGCCAAAGATTTGGAGGAGAAGGACATTTACTGCAGTG
AGAATGAGGGCCAAGAAGAGTCAGGCCTTAATTTCAATATAATTAACTTCAGAGGG
AAAGTAAATATTTCAGGCATACTGACACTTTGCCAGAAAGCATAAAATTCTTAAAATAT
ATTTCAGATATCAGAATCATTGAAGTATTTCCTCCAGGCAAAATTGATATACTTTTTT
CTTATTTAACTTAACATTCTGTAAATGTCTGTAACTTAATAGTATTTATGAAATGGT
TAAGAATTGGTAAATTAGTATTTATTAATGTTATGTTGTGTTCTAATAAAACAAAAA
TAGACAACTGTTC
```

Fig. 2

```
ATG AGG ATG CTT CTG CAT TTG AGT TTG CTA GCT CTT GGA GCT GCC
Met Arg Met Leu Leu His Leu Ser Leu Leu Ala Leu Gly Ala Ala

TAC GTG TAT GCC ATC CCC ACA GAA ATT CCC ACA AGT GCA TTG GTG
Tyr Val Tyr Ala Ile Pro Thr Glu Ile Pro Thr Ser Ala Leu Val

AAA GAG ACC TTG GCA CTG CTT TCT ACT CAT CGA ACT CTG CTG ATA
Lys Glu Thr Leu Ala Leu Leu Ser Thr His Arg Thr Leu Leu Ile

GCC AAT GAG ACT CTG AGG ATT CCT GTT CCT GTA CAT AAA AAT CAC
Ala Asn Glu Thr Leu Arg Ile Pro Val Pro Val His Lys Asn His

CAA CTG TGC ACT GAA TTT CAG GGA ATA GGC ACA CTG GAG
Gln Leu Cys Thr Glu Phe Gln Gly Ile Gly Thr Leu Glu

AGT CAA ACT GTG CAA GGG GGT ACT GTG GAA AGA CTA TTC AAA AAC
Ser Gln Thr Val Gln Gly Gly Thr Val Glu Arg Leu Phe Lys Asn

TTG TCC ATA AAG AAA TAC ATT GAC GGC CAA AAA AAA AAG TGT
Leu Ser Ile Lys Lys Tyr Ile Asp Gly Gln Lys Lys Lys Cys

GGA GAA AGA CGG AGA GTA AAC CAA TTC CTA GAC TAC CTG CAA
Gly Glu Arg Arg Arg Val Asn Gln Phe Leu Asp Tyr Leu Gln

GAG TTT CTT GGT GTA ATG AAC ACC GAG TGG ATA ATA GAA AGT TGA
Glu Phe Leu Gly Val Met Asn Thr Glu Trp Ile Ile Glu Ser STP
```

Fig. 5(a)

| Sequence | Position |
|---|---|
| ATCCTAATCAAGACCCCAGTGAACAGAACTCGACCCTGC | 39 |
| CAAGGCTTGGCATTTCCATTTCAATCACTGTCTTCCCAC | 78 |
| CAGTATTTTCAATTTCTTTTAAGACAGATTAATCTAGCC | 117 |
| ACAGTCATAGTAGAACATAGCCGATCTTGAAAAAAAACA | 156 |
| TTCCCAATATTTATGTATTTTAGCATAAAATTCTGTTTA | 195 |
| GTGGTCTACCTTATACTTTGTTTTGCACACATCTTTTAA | 234 |
| GAGGAAGTTAATTTTCTGATTTTAAGAAATGCAAATGTG | 273 |
| GGGCAATGATGTATTAACCCAAAGATTCCTTCCGTAATA | 312 |
| GAAAATGTTTTAAAGGGGGGAAACAGGGATTTTTATTA | 351 |
| TTAAAAGATAAAAGTAAATTTATTTTTTAAGATATAAGG | 390 |
| CATTGGAAACATTTAGTTTCACGATATGCCATTATTAGG | 429 |
| CATTCTCTATCTGATTGTTAGAAATTATTCATTTCCTCA | 468 |
| AAGACAGACAATAAATTGACTGGGGACGCAGTCTTGTAC | 507 |
| TATGCACTTTCTTTGCCAAAGGCAAACGCAGAACGTTTC | 546 |

```
AGAGCC ATG AGG ATG CTT CTG CAT TTG AGT        576
       Met Arg Met Leu Leu His Leu Ser

TTG CTA GCT CTT GGA GCT GCC TAC GTG TAT        606
Leu Leu Ala Leu Gly Ala Ala Tyr Val Tyr

GCC ATC CCC ACA GAA ATT CCC ACA AGT GCA        636
Ala Ile Pro Thr Glu Ile Pro Thr Ser Ala

TTG GTG AAA GAG ACC TTG GCA CTG CTT TCT        666
Leu Val Lys Glu Thr Leu Ala Leu Leu Ser

ACT CAT CGA ACT CTG CTG ATA GCC AAT GAG        696
Thr His Arg Thr Leu Leu Ile Ala Asn Glu
```

| Sequence | Position |
|---|---|
| GTAATTTTCTTTATGATTCCTACAGTCTGTAAAGTGCAT | 735 |
| AGGTAATCATTTGTGATGGTTCCTTTACTATATATAGAG | 774 |
| ATCTGTTATAAATAATAAGATTCTGAGCACATTAGTACA | 813 |
| TGGGTGATAACTACATCACCAGCAAACATTCTGTTAAAA | 852 |
| GTTATGAATGCTGGTGTGCTGTAAAAATGATTGTATTTC | 891 |

```
CTTTCCTCTCCAG ACT CTG AGG ATT CCT GTT         922
              Thr Leu Arg Ile Pro Val
```

Fig.5(b)

| | |
|---|---|
| CCT GTA CAT AAA AAT GTAAGTTAAATTATGATTC<br>Pro Val His Lys Asn | 956 |
| AGTAAAATGATGGCATGAATAAGTAAATTTCCTGTTTTA | 995 |
| AGCTGTAAATCATTAGTTATCATTGGAACTATTTAATTT | 1034 |
| TCTATATTTTGTTTTCATATGGGTGGCTGTGAATGTCTG | 1073 |
| TACTTATAAATATGAGGAATGACTTTTTATCAAGTAGAA | 1112 |
| TCCTTTAAACAAGTGGATTAGGCTCTTTGGTGATGTTGT | 1151 |
| TAGTTTGCCTTCCCAAAGAGCATCGTGTCAGGATTCTTT | 1190 |
| CCAGAAGGATTCCACACTGAGTGAGAGGTGCGTGCTAGT | 1229 |
| CTCCGTGCAGTTCTGACTCTTTCTCACTCTAACGTGTTT | 1268 |
| CTGAAAGTATTAGCAACTCAGAATTATATTTTTAGAACC | 1307 |
| ATGATCAGTAGACATTAAAATATATAACAAATGCCCTAT | 1346 |
| ATTAATAATTCTGCATACTTAAATAATTATGACTATATG | 1385 |
| ATGGTGTGTATGCATTGAATATGCCTGGTCATATTAAAA | 1424 |
| TGTAAAATATATAGTTTATTAGTCTAAATAGAATAAAAC | 1463 |
| TACCAGCTAGAACTGTAGAAACACATTGATATGAGTTTA | 1502 |
| ATGTATAATGCATTACACTTCCAAAACATTTTTTTCCAG | 1541 |
| TTACATAATTAAGTTATATCCTTTATAAAACTCCTCAGT | 1580 |
| AATCATATAAGCTTCATCTACTTTTTGAAAATTTTATCT | 1619 |
| TAATATGTGGTGGTTTGTTGCCTAGAAAACAAACAAAAA | 1658 |
| ACTCTTTGGAGAAGGGAACTCATGTAAATACCACAAAAC | 1697 |
| AAAGCCTAACTTTGTGGACCAAAATTGTTTTAATAATTA | 1736 |
| TTTTTTAATTGATGAATTAAAAAGTATATATATTTATTG | 1775 |
| TGTACAATATGATGTTTTGAAGTATGTATACATTGCAGA | 1814 |
| ATGGACAATGGACCAAATTTTTATACCTTGTCTTGATTA | 1853 |
| TTTGCATTTTAAAAATTTTCCTCATTTAG CAC CAA<br>His Gln | 1888 |
| CTG TGC ACT GAA GAA ATC TTT CAG GGA ATA<br>Leu Cys Thr Glu Glu Ile Phe Gln Gly Ile | 1918 |
| GGC ACA CTG GAG AGT CAA ACT GTG CAA GGG<br>Gly Thr Leu Glu Ser Gln Thr Val Gln Gly | 1948 |

Fig. 5(c)

```
GGT ACT GTG GAA AGA CTA TTC AAA AAC TTG    1978
Gly Thr Val Glu Arg Leu Phe Lys Asn Leu

TCC TTA ATA AAG AAA TAC ATT GAC GGC CAA    2008
Ser Leu Ile Lys Lys Tyr Ile Asp Gly Gln

AAA GTAAGTTACACACATTCAATGGAAGCTATATTTGT    2046
Lys

CCTGGCTGTGCCTATTTCTATGGAATTGACAGTTTCCTG   2085

TAATACCTATTGTCATTTTTCTTTTTTCACAGAAA AAG   2123
                                    Lys Lys

TGT GGA GAA GAA AGA CGG AGA GTA AAC CAA    2153
Cys Gly Glu Glu Arg Arg Arg Val Asn Gln

TTC CTA GAC TAC CTG CAA GAG TTT CTT GGT    2183
Phe Leu Asp Tyr Leu Gln Glu Phe Leu Gly

GTA ATG AAC ACC GAG TGG ATA ATA GAA AGT    2213
Val Met Asn Thr Glu Trp Ile Ile Glu Ser

TGAGACTAAACTGGTTTGTTGCAGCCAAAGATTTTGGAG   2252
***

GAGAAGGACATTTTACTGCAGTGAGAATGAGGGCCAAGA   2291

AAGAGTCAGGCCTTAATTTTCAATATAATTTAACTTCAG   2330

AGGGAAAGTAAATATTTCAGGCATACTGACACTTTGCCA   2369

GAAAGCATAAAATTCTTAAAATATATTTCAGATATCAGA   2408

ATCATTGAAGTATTTTCCTCCAGGCAAAATTGATATACT   2447

TTTTTCTTATTTAACTTAACATTCTGTAAAATGTCTGTT   2486

AACTTAATAGTATTTATGAAATGGTTAAGAATTTGGTAA   2525

ATTAGTATTTATTTAATGTTATGTTGTGTTCTAATAAAA   2564

CAAAAATAGACAACTGTTCAATTTGCTGCTGGCCTCTGT   2603

CCTTAGCAATTTGAAGTTAGCACAGTCCATTGAGTACAT   2642

GCCCAGTTTGGAGGAAGGGTCTGAGCACATGTGGCTGAG   2681

CATCCCCATTTCTCTGGAGAAGTCTCAAGGTTGCAAGGC   2720

ACACCAGAGGTGGAAGTGATCTAGCAGGACTTAGTGGGG   2759

ATGTGGGGAGCAGGGACACAGGCAGGAGGTGAACCTGGT   2798

TTTCTCTCTACAGTATATCCAGAACCTGGGATGGTCGAA   2837

GGGTAAATGGTAGGGAATAAATGAATGAATGTCGTTTCC   2876
```

Fig. 5 (d)

| | |
|---|---|
| AAGATGATTGTAGAACTAAAATGAGTTGTAAGCTCCCCT | 2915 |
| GGAAGAAGGGATGTGGAACCTGTAACTAGGTTCCTGCCC | 2954 |
| AGCCTGTGAGAAGAATTTGGCAGATCATCTCATTGCCAG | 2993 |
| TATAGAGAGGAAGCCAGAAACCCTCTCTGCCAAGGCCTG | 3032 |
| CAGGGGTTCTTACCACCTGACCCTGCACCATAACAAAAG | 3071 |
| GACAGAGAGACATGGTAGGGCAGTCCCATTAGAAAGACT | 3110 |
| GAGTTCCGTATTCCCGGGGCAGGGCAGCACCAGGCCGCA | 3149 |
| CAACATCCATTCTGCCTGCTTATGGCTATCAGTAGCATC | 3188 |
| ACTAGAGATTCTTCTGTTTGAGAAAACTTCTCTCAAGGA | 3227 |
| TCC | 3230 |

Fig. 11

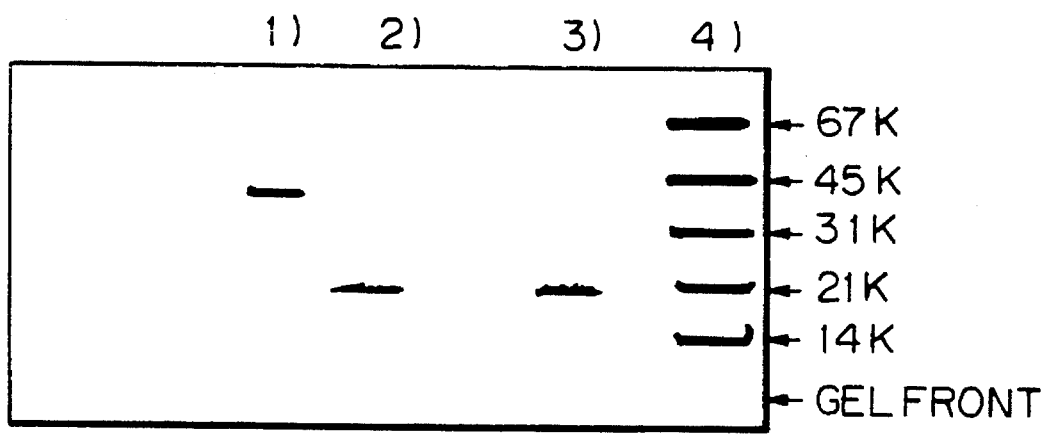

Fig. 7

M13mp19 BamHI-PstI-Gtail- ATGCACTTTCTTTGCCAAAGGCAAACGCAGAACGTTTCAGAGCC

ATG AGG ATG CTT CTG CAT TTG AGT TTG CTA GCT CTT GGA GCT GCC

TAC GTG TAT GCC ATC CCC ACA GAA ATT CCC ACA AGT GCA TTG GTG

AAA GAG ACC TTG GCA CTG CTT TCT ACT CAT CGA ACT CTG CTG ATA

GCC AAT GAG ACT CTG AGG ATT CCT GTT CCT GTA CAT AAA AAT CAC

CAA CTG TGC ACT GAA GAA ATC TTT CAG GGA ATA GGC ACA CTG GAG

AGT CAA ACT GTG CAA GGG GGT ACT GTG GAA AGA CTA TTC AAA AAC

TTG TCC TTA ATA AAG AAA TAC ATT GAC GGC CAA AAA AAA AAG TGT

GGA GAA GAA AGA CGG AGA GTA AAC CAA TTC CTA GAC TAC CTG CAA

GAG TTT CTT GGT GTA ATG AAC ACC GAG TGG ATA ATA GAA AGT TGA

GACTAAACTGGTTTGTTGCAGCCAAAGATTTTGGAGGAGAAGGACATTTTACTGCAG → M13mp19
                                                           PstI

HUMAN B-CELL DIFFERENTIATION FACTOR AND PROCESS OF PRODUCING SAID FACTOR

This is a division of application No. 07/099,467, filed Sep. 21, 1987 now U.S. Pat. No. 5,324,640.

FIELD OF THE INVENTION

The present invention relates to the human B-cell differentiation factor and process of producing said factor.

The B-cell differentiation factor, which is abbreviated as BCDF [please note, in the case of a mouse (BCDF), it is also designated as T-cell replacing factor (TRF)], is composed of a polypeptide which is secreted by the cells of T-cell line and acts directly on B-cells to induce their differentiation into antibody-secreting cells.

Antibodies function to react with foreign substances such as bacteria or viruses that enter a living body, as well as cancer Cells, and thereby inactivate or eliminate them. The B-cell differentiation factor induces differentiation of a B-cell clone specific to a particular antigen (foreign substance), that is, a B-cell clone is sensitized with a particular antigen to form antibody-secreting cells which secrete antibodies against said antigen. Therefore, BCDF is a useful substance for the treatment of various infections and cancers. In other words, BCDF is expected to be useful not only in the diagnosis or treatment of immuno-deficiency diseases, etc., which are supposed to occur due to the deficiency of this factor in a living body, but also in the treatment of various infections and cancers.

The activity of BCDF is reported to be species-specific. Therefore, in order to use this factor for the treatment or diagnosis of aforementioned diseases, infections, and cancers, it is desirable to use BCDF originating from human cells.

PRIOR ART

Several studies have been conducted on BCDF or TRF. BCDF (or TRF) in mice was first reported by R. W. Dutton et al. [Prog. Immunol., 1, 355 (1971)] and A. Schimpl and E. Wecker [Nature, 237, 15 (1972)]. Later, Geha, R. S., et al. [J. Exp. Med., 138, 1230 (1973)], Fauci, A. S., et al. [J. Immunol., 117, 2100 (1976)]; Hirano, T., et al. (J. Immunol., 119, 1235 (1977)] reported that a counterpart of mouse BCDF (or TRY) is also present in humans. However, as the structure of the substance has not been fully clarified, and genes associated with the substance are unknown, [Kishimoto, T., Ann. Rev. Immunol., 3, 133 (1985)] the matter is still controversial.

So far, human BCDF has been obtained from a culture supernatant of normal human T-cells, first isolated from human peripheral blood and then stimulated with mitogen [Hirano, T., et al., J. Immunol., 126, 517 (1981) and Ralph, P., et al., J. Immunol., 137, 1858 (1984)]. In the above-mentioned article, Ralph, P., et al. reported a concentration of BCDF with a factor of about 11,000 resulting from 3 liters of a supernatant of cultured mitogen-stimulated normal human T-cells using such techniques as ammonium sulfate precipitation, DEAE cellulose column chromatography (DE-52), gel filtration column chromatography (AcA44), affinity chromatography using blue agarose and red agarose, reverse-phase high performance liquid chromatography, etc. The molecular weight of BCDF thus obtained was determined by gel-filtration chromatography at about 20,000, but this method did not lead to pure BCDF, and the amount obtained was very small (from 3 liters of the supernatant, only 4.2 µg was obtained). Okada, M., et al. reported a method for obtaining human BCDF from a culture medium of a fused human T-cell strain, obtained by fusing normal human T-cells with cells of a human T-cell strain CEM-AG$^R$ [J. Exp. Med., 157, 583 (1983)]. In general, cells of a fused human cell strain tend to lose their ability to secrete substances during subculture; therefore, the above method does not appear to be suitable for the practical production of such substances.

There are two types of human BCDF, namely, BCDF I and BCDF II. Respective properties of these two are reported as in the following [Teranishi, T., et al., J. Immunol., 128, 1903 (1982) and Hirano, T., et al., J. Immunol., 132, 229 (1984)]:

BCDF I:
  Molecular weight: 20,000 (gel filtration method)
  PI: 6.5–8.0
    Action: induce the differentiation of Staphylococcus aureus Cowan I (SAC)—stimulated B-cells into immunoglobulin (Ig)—secreting cells.

BCDF II:
  Molecular weight: 22,000, 36,000 (gel filtration method)
  PI: 5–6
    Action: 1) induce B-lymphoblastoid cells (B-LCL), transformed by EB virus, to secrete IgG.
    2) augment differentiation of SAC-stimulated B-cells into Ig-secreting cells in the presence of BCDF I (BCDF II alone does not have this activity).

Recently, a method for the production of human BCDF using a human T-cell line named VT-1, which was transformed by human T-cell leukemia virus (HTLV), has been reported (Chuzo Kishimoto and Toshio Hirano, Japanese Patent Laid-Open Nos. 115024/1986 and 115025/1986). The inventors of these patent applications purified BCDF from 10 liters of serum-free culture supernatant of VT-1 cells with a factor of 1042, employing ultrafiltration, AcA-34 gel filtration column chromatography, chromato-focusing, and reverse-phase chromatography (yield: 1.8%), and reported that the molecular weight of human BCDF is $3.5 \pm 0.5 \times 10^4$ daltons (gel filtration method) or $2.2 \pm 0.2 \times 10^5$ daltons (SDS polyacrylamide electrophoresis method), that its isoelectric point is 4.9–5.1, and that the partial amino acid sequence at its N-terminal is Pro-Val-Pro-Pro-Gly-Glu-Asp-Ser-Lys-Asp-Val-Ala-Ala-. This purified BCDF obtained by them appears to be BCDF II, considering that they employed CESS cells transformed by EB virus for the determination of the BCDF activity based on the amount of IgG secretion in the CESS cells when they examined the degree of purification, and also considering its molecular weight and PI values. However, the molecular weight of human BCDF obtained by Ralph, P., et al. mentioned above was determined at 20,000 daltons by gel filtration method. This BCDF thus appears to be BCDF I, but its structure and other physicochemical properties have not been revealed. The method for producing BCDF using VT-1 cells, as described above is more improved than the method using cells from human peripheral blood or human fused T-cells as described earlier, but the amount of BCDF obtained from a large amount of culture supernatant is very small, and this method both uses HTLV-infected cells as their starting material; thus, this method is not suitable for the industrial production of pharmaceuticals.

As described above, not only the structure but also the physicochemical properties and functions are not fully revealed for human BCDF. In addition, prior arts have not enabled large scale production for practical purposes.

SUMMARY OF THE INVENTION

The present invention fully utilizes present genetic recombinant techniques, and intends to solve the above-mentioned problems.

In other words, the present invention intends to provide the possibility of a large scale production of BCDF and its application to pharmaceuticals. A recombinant DNA technique is used, through the isolation of mRNA of BCDF from cells which secrete large amount of human BCDF, elucidation of the DNA nucleotide sequence of the BCDF cDNA as well as the chromosomal BCDF gene which govern the BCDF secretion, and elucidation of the molecular structure of BCDF (amino acid sequence).

The human B-cell differentiation factor mentioned in the present invention corresponds to BCDF I, but similar methods to those employed in the present invention will enable elucidation of the structure of BCDF II as well.

BRIEF DESCRIPTION OF THE DRAWINGS

FIG. 1 shows the nucleotide sequence of cDNA which is inserted in the plasmid ph-IL-5-30 and which includes the human BCDF cDNA sequence.

FIG. 2 shows the human BCDF polypeptide encoding region including the leader peptide in the nucleotide sequence as shown in FIG. 1. The amino acid sequence coded for by said region is also shown in this figure.

FIGS. 5(a)–5(d) shows the entire nucleotide sequence of the human BCDF chromosomal gene (3.2 kb BamHI fragment).

FIG. 7 shows the cDNA of human BCDF which was inserted between the BamHI and PstI sites of the phage M13mp19DNA.

FIG. 11 shows the polyacrylamide gel electrophoresis pattern of the purified recombinant human BCDF.

DETAILED DESCRIPTION OF THE INVENTION

Figure 3:
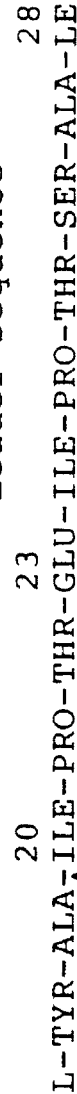
FIG. 3 is a repetition of the amino acid sequence of human BCDF as shown in FIG. 2, the sequences of the leader peptide and the mature human BCDF being clearly specified here.

The human BCDF cDNA of the present invention can be obtained, as detailed below, by using, as a probe, a BamHI-AccI fragment (containing the entire coding sequence of mouse B-cell differentiation factor) of a plasmid pSP6K-mTRF23 previously prepared by the present inventors (Specification of Japanese Patent Application No. 157227/1986), in which a mouse B-cell differentiation factor cDNA is cloned. Escherichia coli into which the plasmid pSP6K-mTRF23 has been introduced (HB101/pSP6K-mTRF23), is named SBM285 and has been deposited at the Fermentation Research Institute, Japan with Accession Number FERM P-8828.

First, to ascertain whether a nucleotide sequence capable of hybridizing with mouse B-cell differentiation factor exists in human chromosome DNA, DNA is extracted from for example, normal human placenta digested with PvuII or PstI, and the above-mentioned BamHI-AccI fragment of the plasmid pSP6K-mTRF23 is labelled with $^{32}P$ by the nick-translation method, followed by the Southern blot hybridization using the labelled fragment as a probe. When the DNA from human placenta cells is digested with PvuII, a DNA fragment of 3.0 kb hybridizes with the above-mentioned probe, but when the DNA is digested with PstI, a DNA fragment of 4.1 kb hybridizes with the same. This result demonstrates that a human chromosome contains a DNA segment with a nucleotide sequence similar to that of mouse B-cell differentiation factor. The result also shows the possibility of cloning human BCDF cDNA using the above-mentioned probe.

On the basis of the above findings, cDNA library of human BCDF can be constructed as described in the following. From the cultured cells of human T-cell line ATL-2, which was established by Maeda, M., et al. [J. Exp. Med., 162, 2169 (1985)], poly (A)$^+$RNA is prepared according to the routine method [Nikaido, T., et al., Nature, 311, 631 (1984)] and then a cDNA library is constructed following the Okayama-Berg method in which pCD vector is used [Okayama, H. and Berg, P., Mol. Cell Biol., 3, 280 (1983)]. After plasmid DNAs are separated, the DNAs are digested with SalI or BamHI followed by Southern blot hybridization [Southern, E. M., J. Mol. Biol., 98, 503 (1975)] with the above-mentioned probe ($^{32}P$ labelled BamHI-AccI DNA fragment) to examine that this library contains the human counterpart to the mouse BCDF cDNA. A discrete band corresponding to cDNA of about 4.1 kb is detected in digestion with SalI and of about 1 kb in digestion with BamHI. After screening of about $5 \times 10^4$ clones according to the routine method [Hanahan, D. and Meserlson, M., Gene, 10, 63 (1980)], 29 clones which hybridize to mouse cNDA probe and are distinguishable from each other were obtained. Clones found to be positive are considered to contain a plasmid with cDNA gene of human BCDF. A plasmid contained in one (ph-IL-5-30) of the clones obtained in this way was named pCDVTRF, and a transformed bacteria (HB101/pCDVTRF), which was produced by introducing said plasmid into Escherichia coli HB101 strain, has been named SBM286, and has been deposited at Fermentation Research Institute, Japan with Accession Number FERM BP-1171.

Whether or not the plasmid of clones found to be positive, truly contain the clones of human BCDF cDNA, similar to mouse B-cell differentiation factor, can be ascertained by the restriction analysis and by hybridization with the said probe. The nucleotide sequence of the DNA, and also whether or not the DNA is coding for the polypeptide with human BCDF activity can both be ascertained as described in the following.

According to the routine method, the restriction map of the plasmid (ph-IL-5-30) of the clone is examined, and the cDNA which has been inserted into said plasmid and which contain human BCDF cDNA gene is recloned at the BamHI site of pUC18 plasmid, and the nucleotide sequence of the said cDNA is determined by the dideoxy method [Sanger, F., et al., Proc. Natl. Acad. Sci. USA, 74, 5463 (1977)]. According to the present inventors' study, the nucleotide sequence of cDNA containing human BCDF cDNA was determined as shown in FIG. 1 following the above-described method.

Determination of human BCDF coding region

The existence of the human BCDF encoding region in the cDNA nucleotide sequence obtained above is confirmed as follows.

The open reading frame of this nucleotide sequence is examined, and at the same time, the human B-cell differentiation factor (BCDF) polypeptide encoding region is located by comparing the sequence with that of the mouse B-cell differentiation factor encoding region which has already been determined by the present inventors. The amino acid sequence of the polypeptide is then determined (FIG. 2). From the amino acid sequence encoded by that region, and from the fact that human BCDF are proteins secreted extracellularly, the precursor of human BCDF polypeptide is considered to be composed of 134 amino acids, including a signal peptide or leader peptide consisting of 19 amino acids starting from the N-terminal of the polypeptide (FIG. 3). In other words, the region between the 20th amino acid and the 134th amino acid from the N-terminal in the amino acid sequence shown in FIG. 3 is considered to be the mature human BCDF polypeptide. Considering that the amino acid sequence of the precursor has two possible N-glycosylation sites (the 47th and 90th Asn residues) and at least one possible O-glycosylation site (the 22nd Thr) where saccharide chains may be bound, the molecular weight of the said mature human BCDF polypeptide (13,149) is consistent with that reported for human BCDF I (about 20,000, including possible saccharide chains). The Met (Methionine) residue at the N-terminal of the polypeptide shown in FIG. 3 may be formylated or acetylated, or the whole Met residues may be eliminated during post-translational modification process. The amino acid at the N-terminal of the said mature BCDF polypeptide may also be acetylated in a similar process.

The cDNA inserted in said plasmid ph-IL-5-30, i.e. the DNA identified as described above, may of course be checked for its ability of encoding the polypeptide having a human BCDF activity by incorporating it into an appropriate expression vector which is then used to transfact appropriate host cells to produce the polypeptide. However, this check for said ability may be more appropriately conducted as described in the following.

First, the BamHI DNA fragment containing entire human BCDF cDNA inserted in the plasmid ph-IL-5-30 is recloned in pSP64 vector. The pSP64 is an improved vector as an inserted foreign gene can be expressed only under the influence of the SP6 promotor, and is capable of synthesizing mRNA of the inserted foreign gene in the presence of SP6 RNA polymerase in vitro [Krieg, P. A. and Melton, D. A., Nucl. Acid. Res., 12, 7057 (1984), and Kanarska, M. M. et al., Cell, 38, 731 (1984)]. In the next step, the mRNA solution prepared in vitro from said cDNA, is injected into Xenopus oocyte for culture. The BCDF activity of a translation product (peptide) from the mRNA secreted in the culture supernatant is determined. The human BCDF activity (especially human BCDF I activity) is determined, as was described earlier, by examining the capability of the substance to induce IgM production in human B-cells stimulated with Staphylococcus aureus Cowan I (SAC) and comparing the capability with that of a control. In this way, the cDNA was confirmed to be coding for the polypeptide with the human BCDF activity, and at the same time, the possibility of large-scale production of human BCDF polypeptide using DNA according to the present invention was shown, as was described in the appended claims.

Expression of human BCDF

It is possible in accordance with the present invention, that the nucleotide sequence prepared as described above is used to produce human BCDF.

For example, if cDNA is used as the human BCDF encoding gene, an expression vector is prepared by using an appropriate promotor, for example, the promotor from SV 40, which is inserted at the 5' upstream of the cDNA. Said expression vector is then introduced into appropriate cells such as yeast cells, E. coli cells, or animal cells such as COS-1 or CHO whereby a protein capable of differentiating human B-cells is produced. In this method it is preferred that the cDNA region used codes for the precursor protein, although the cDNA region which codes for the mature protein may also be used conveniently. In addition, in order to facilitate the introduction of the foreign promotor, an appropriate restriction site such as the HindIII site may be provided to the expression vector at the immediate upstream of the DNA coding for the purposed protein by an appropriate method such as the site directed mutagenesis method.

Alternatively, in accordance with the present invention, it is also possible to prepare from human chromosomes the human BCDF gene which contains introns and this chromosomal human BCDF gene may be used in place of the cDNA to produce the desired human B-cell differentiation protein.

According to this alternative, a DNA fragment containing a human BCDF gene is separated from a human gene library, for example the human gene library of Maniatis, using the foregoing cDNA as a probe. An expression vector is subsequently constructed by inserting an appropriate promotor upstream of the DNA region encoding human BCDF similarly as the above described alternative. The expression vector thus constructed is then used to transfact host cells which are cultured in order to have them produce human BCDF efficiently. The host cells used here are selected from yeast cells or animal cells having splicing ability.

An E. coli strain (HB101/pdKCR-hIL-5gene) which has an expression vector wherein human chromosomal BCDF gene is incorporated (pdKCR-hIL-5gene) is named SBM 293 and has been deposited at Fermentation Research Institute, Japan with the Accession Number FERM BP-1477.

Purification of recombinant human BCDF

The recombinant human BCDF produced by the transfected cells, constructed as explained, can be purified through an appropriate process, for example, using an affinity chromatography with a monoclonal antibody, a gel filtration and a reverse phase high performance liquid chromatography.

Figure 12:
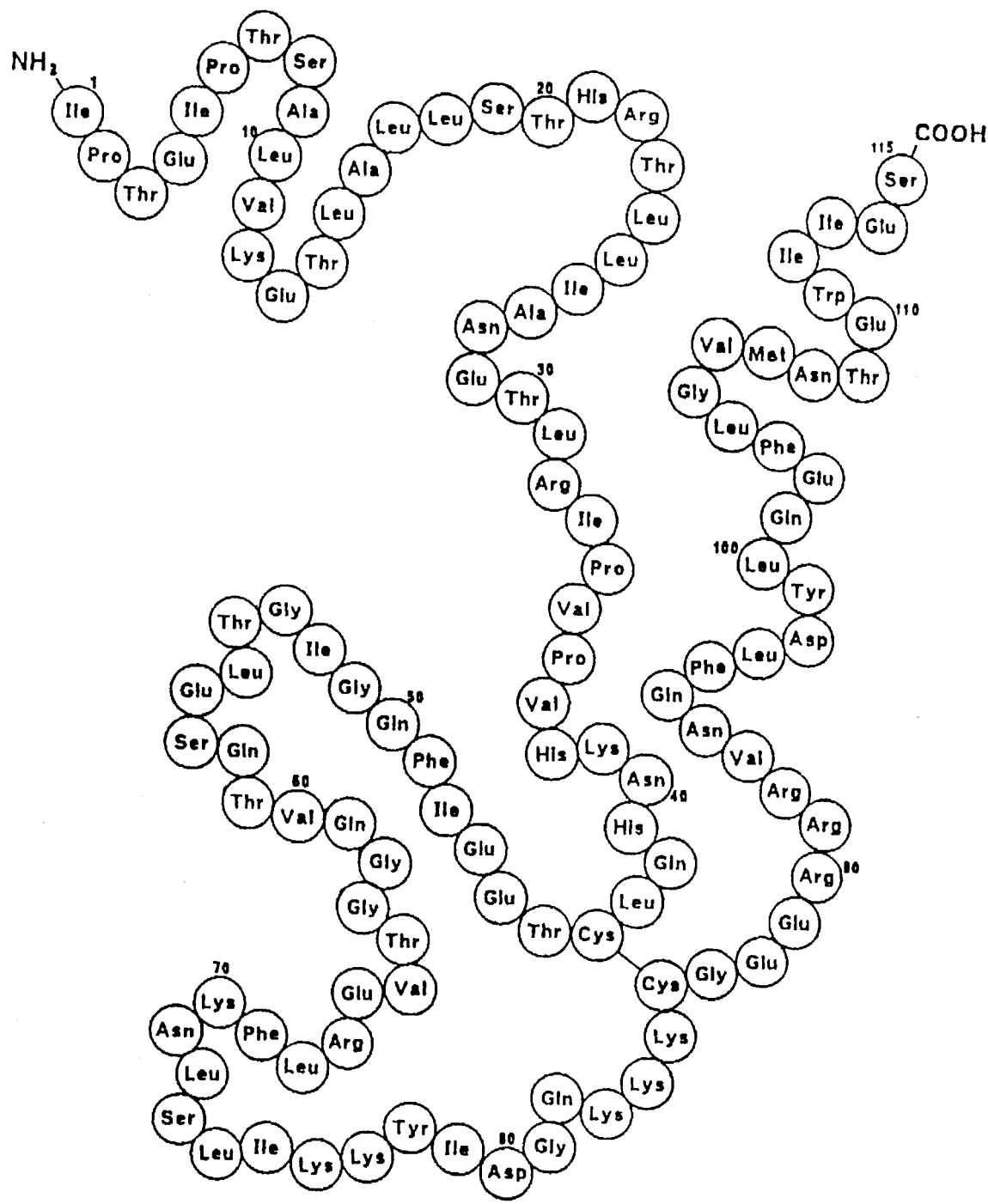
FIG. 12 shows the speculated two dimensional amino acid arrangement of the polypeptide portion of the mature recombinant human BCDF monomer.

In accordance with the present invention, the recombinant human BCDF, thus purified and isolated, is subjected to analysis with respect to the amino acid sequence and the electrophoresis properties, and it has been determined that the polypeptide portion structure of the mature human BCDF has the sequence between the 20th Ile to the 134th Ser (see FIG. 3) as explained before, based on the results of the analysis and the nucleotide sequence of the human BCDF encoding gene as determined above. The inventors have presented a speculated two dimensional arrangement of the peptide sequence which is shown in FIG. 12.

The present invention is illustrated further by the following examples.

EXAMPLES (1) Identification of human BCDF gene

The present inventors identified the gene, i.e., DNA nucleotide sequence, governing the mouse BCDF (TRF) production (specification of Japanese Patent Application No. 157227/1986). The mouse TRF coded for by this gene was revealed to have TRF activities namely, [1] an activity to differentiate mouse chronic B leukemia cells ($BCL_1$) into antibody-secreting cells, 2) an activity to differentiate the B-cells in the spleen of a mouse sensitized to an antigen (DNP-KLH), into a specific antibody (anti-DNP-IgG) producing cells by the stimulation of an antigan (DNP-ovalbumin), and 3) an activity to induce IgM secretion in B-cell blast activated in vivo, and BCDF II activities namely, [1] an acceleration of the division of $BCL_1$ cells, 2) an acceleration of division of resting B-cells stimulated with dextran sulfate]. The plasmid pSP6K-mTRF23 containing cDNA complementary to mouse TRF mRNA was digested with BamHI and AccI, and a BamHI-AccI fragment consisting of 654 bp was separated. This fragment, which contained the entire coding region for mouse BCDF (TRF), was labelled with $^{32}P$ by nick-translation, and the labelled fragment used as a probe, the Southern blot hybridization of human chromosome DNA was conducted by the known method [Southern, E. M., J. Mol. Biol., 98, 503 (1975)]. The human chromosome DNA used here was extracted from normal human placenta by the method of Yaoita, Y. and Honjo, T. (Biomed. Res., 1, 164 (1980), and 2 μg each was digested with either PvuII or PstI, respectively, and subjected to electrophoresis with 0.6% agarose gel for the Southern blot hybridization. After the electrophoresis, DNA in the gel was transferred onto a nitro-cellulose filter [Schleicher & Sch üel (Dassel)], and allowed to hybridize with the said probe. The washing was conducted under conditions of 2×SSC (SSC: 0.15M NaCl-0.015M sodium citrate) containing 0.1% SDS at 50° C. for 45 minutes. In the case of PvuII digestion, a DNA fragment of 3.0 kb, and in the case of PstI digestion, a DNA fragment of 4.1 kb was respectively found to hybridize with the mouse BCDF probe. Because this probe is known to hybridized with mouse chromosome DNA fragment under more stringent conditions, it was concluded that human chromosome DNA has a highly homologous, if not entirely equal, sequence to that found in the mouse BCDF (TRF) cNDA, and that the screening of cDNA clone of human BCDF would be possible using this probe.

(2) Separation of human BCDF cDNA clone

A cDNA library of human BCDF was constructed as described in the following:

Human T cell line ATL-2 established by M. Maeda, et al., using the blood of an adult T cell leukemic patient [J. Exp. Mad., 162, 2169 (1985)] was cultured in the medium of RPMI 1640+ 10% fetal bovine serum at 37° C. in 5% $CO_2$ to collect the cells. From the cells, poly $(A)^+RNA$ was prepared by the routine method [Nikaido, T., et al., Nature, 311, 631 (1984)]. Using 3 μg of this poly $(A)^+RNA$, cDNA library was constructed. The method employed involved the use of pCD vector in accordance with Okayama-Berg method [Okayama, H. and Berg, P., Mol. Cell Boil., 3, 280 (1983)], and $2 \times 10^5$ independent cDNA clones were obtained as transformed Escherichia coli (HB101 strain).

In order to examine whether a cDNA which corresponds to human BCDF cNDA is present in the $2 \times 10^5$ cDNA clones, the plasmid DNA was prepared from the entire mixture of transformed cells. Two μg each of DNA was digested with either SalI or BamHI, respectively, and the Southern blot hybridization was conducted by the above-mentioned method. The result showed that in the case of SalI digestion, which gave one cut to the sequence of pCD vector, a DNA fragment of 4.1 kb hybridized, while in the case of BamHI digestion, which cleaves at the proximities of the both ends of the inserted cDNA, a DNA fragment of 1.0 kb hybridized.

From these results, it was suggested that the cDNA library contained a clone whose DNA nucleotide sequence corresponds to the human counterpart to the mouse BCDF cDNA. Therefore, using the aforementioned mouse probe, the said $2'10^5$ cDNA clones were screened according to the routine colony hybridization [Hanahan, D. and Meserlson, M., Gene, 10, 63 (1980)]. The results of the screening showed that 29 clones hybridized with mouse BCDF (TRF) cDNA probe. The endonuclease cleavage map of the plasmid DNA of these 29 clones, and the Southern blot hybridization of DNA fragment digested with endonuclease using the said probe, showed that the 29 clones were identical.

(3) Nucleotide sequencing of human BCDF cDNA and amino acid sequence of human BCDF cDNA polypeptide One of the above-mentioned 29 clones, ph. IL-5-30 was examined in more detail. After examining the endonuclease cleavage map by the routine method, the cDNA inserted into ph-IL-5-30 was subcloned at BamHI site of pUC18 plasmid, and the DNA nucleotide sequence of the cDNA was determined the routine dideoxy method [Sanger, F., et al., Proc. Natl. Acad. Sci. USA, 74, 5463 (1977)]. The result showed that the inserted cDNA is 816 base-pairs long, excluding the poly A tail.

By comparing the result with that of the mouse BCDF (TRF) DNA nucleotide sequence, the coding region of the human BCDF was determined, and the precursor of human BCDF was revealed to consist of 134 amino acid residues. As the human BCDF is secreted outside of the T cell, these amino acid residues are expected to contain a signal sequence at the N-terminal. Therefore, the mature human BCDF is considered to be a molecule containing a polypeptide consisting of the region between the 20th amino acid residue and the 134th amino acid residue from the N-terminal in said 134 amino acid sequence. The amino acid sequence has two possible N-glycosylation sites (Asn at the 47th and 90th amino acid residues in FIG. 3) and at least one O-glycosylation site (Thr at the 22nd amino acid residue in FIG. 3). If the molecular weight of one or more saccharide chains which may be bound here and that of this polypeptide (13,149, when the segment between the 20th amino acid residue and the 134th residue is considered) are added, the resulting molecular weight is consistent with the value, 20,000, which was reported for BCDF I.

When compared with the mouse BCDF (TRF), the precursor of human BCDF is one amino acid residue longer. Two possible glycosylation sites in the human BCDF coincide with the first and the third possible N-glycosylation sites in the mouse BCDF. Of the three cysteine residues in mouse BCDF (TRF), the two on the C-terminal side are also conserved in human BCDF. The nucleotide and amino acid sequences of the coding region of the human and mouse BCDF are 78% and 70% homologous, respectively. Using the PstI fragment (515 bp) of ph-IL-5-30 labelled with $^{32}$P by the nick-translation as a probe, the DNA fragments of the said human chromosome DNA digested with PvuII or PstI were subjected to the Southern blot hybridization as described before. The result was similar to the case when the mouse BCDF probe was used, namely, fragments of 4.1 kb and 3.0 kb underwent hybridization, respectively. When the human probe was used, sufficient hybridization was made even when the washing condition was as stringent as 0.1× SSC-0.1% SDS, 65° C., 45 minutes. When the ATL-2 poly (A)$^+$RNA was subjected to the Northern blot hybridization according to the routine method [Thomas, D. D., Proc. Natl. Acad. Sci. USA, 77, 5201 (1980)] using said human probe, only one band of 1.0 kb was observed. This demonstrates that the human BCDF gene identified by the present inventors in the human chromosome DNA sequence, is a homologous gene specific to mouse BCDF (TRF) gene, and that only one mRNA is transcribed from this human BCDF gene.

(4) Determination of human BCDF activity

The polypeptide or the substance comprising said polypeptide, whose secretion is governed by the human BCDF gene identified as described above, was shown to have human BCDF I activity by the method described below. A DNA fragment containing the entire human BCDF cDNA insert and a small vector part was removed from the plasmid ph-IL-5-30 using BamHI and the fragment was recloned in pSP64 plasmid vector. After said plasmid was digested with SalI, it was allowed to synthesize mRNA in vitro using SP6 RNA polymerase [Krieg, P. A. and Melton, D. A., Nucleic Acid Res., 12, 7057 (1984); and Konarska, M. M., et al., Cell, 38, 731 (1984)]. The mRNA solution thus prepared was injected into Xenopus oocyte, and after being cultured for 48 hours at 20° C., the product secreted in the culture solution was collected and centrifuged, and then the supernatant was concentrated 4 folds using a concentration apparatus (Centricon 10; manufactured by Amicon). The concentrated solution was used as human recombinant BCDF in the following experiments. Whether or not this human recombinant BCDF has BCDF I activity was examined by studying its capability to induce IgM production in human B-cells stimulated with SAC.

Human B-cells enriched fraction was prepared from normal human blood according to the method of Saiki, O. and Ralph, P. [Eur. J. Immunol., 13, 31 (1984)], and 1'10$^5$ cells/100 μl of cells were stimulated with SAC (0.001–0.0025%). The human recombinant BCDF was added so that its concentration became 15%, which was then cultured at 37° C. for 6 days under 5% $CO_2$. The amount of IgM in the culture supernatant was determined using an enzyme immunoassay kit to be 110 ng/well. The amount in the control was about 50 ng/well. The significant induction of IgM production by the recombinant BCDF was demonstrated. This induction was augmented to 135 ng/well by the addition of IL-3 (50 U/ml). The reason why the control showed IgM production seemed to arise from the difficulty of obtaining a B-cell fraction which is completely free from T-cells.

(5) Isolation and identification of the chromosomal gene of human BCDF

In (1) of the Example, the applicant showed the existence of a human BCDF gene in the chromosome of normal human placental cells. They have also isolated human BCDF gene from other sources as follows.

Specifically, the selected sources were Charon 4A phage library containing AluI-HaeIII partial digests of human fetal liver DNA (Maniartis, T., et al., Cell, 15, 687–702, 1978), Charon 4A phage library containing EcoRI partial digests of human placental DNA (prepared in accordance with Yaoita, Y. and Honjo, T., Biomed. Res. 1, 164, 1980) and Charon 4A phage library containing EcoRI partial digests of human IgE-producing myeloma cell line 266B1DNA (Nishida, Y., et al., Proc. Natl. Acad. Sci, USA, 79, 3833 837, 1982).

These three libraries were used to screen the phage for the existence of human BCDF gene in accordance with the method of Becton, W. D. and Davis, R. W. (Science, 196, 180–182, 1977). The 515 bp PstI-PstI fragment of the above-described human BCDF cDNA was used as the probe. The screening among 5×10$^5$ phage plaques of the each library from fetal liver, placenta and myeloma resulted in three clones named λ12 (from fetal liver libraries), λ22 (from placental library) and λ38 (from myeloma library).

Figure 4:
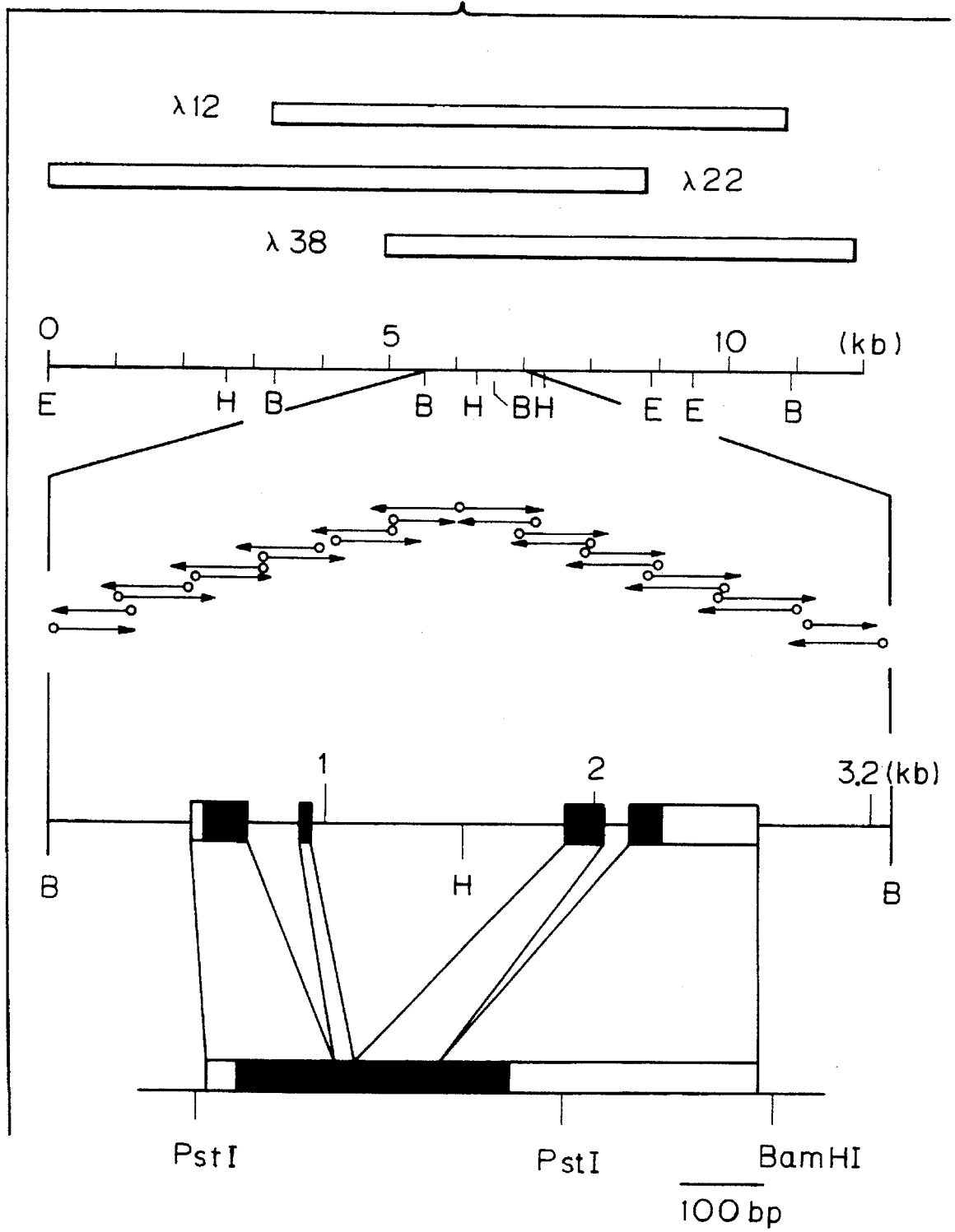
FIG. 4 shows the strategy used for the sequence analysis of the human BCDF gene.

The restriction enzyme cleavage mapping of the obtained three clones were subsequently determined and the Southern blot hybridization analysis was conducted using a PstI-PstI fragment of human BCDF cDNA as a probe. The strategy in the analysis and the location of human BCDF gene are shown in FIG. 4, wherein E, H and B represent the restriction site of EcoRI, HindIII and BamHI respectively and the closed boxes represent coding regions (exons). The analysis showed that the inserts of the isolated three clones overlapped with each other and commonly contained the identical 3.2 kb BamHI fragment as shown in FIG. 4, which was the only fragment hybridized with the above probe. Therefore, this fragment was thought to include all the exons coding for human BCDF. So the 3.2 kb BamHI fragment was separated and then digested with HindIII to cut it into two 1.6 kb fragments. These two fragments were respectively subcloned into pUC 18 plasmid vector. The plasmids containing the cloned two 1.6 kb respectively were digested from both ends by exonucleases III and VII to obtain a series of unidirectional deletion mutant clones. The nucleotide sequences of the inserts of said mutant plasmids were determined by the dideoxy chain-termination method in accordance with the routine method [Sanger, F., et al., Proc. Natl. Acad. Sci. USA, 74, 5463–5469 (1977)]. The restriction endonuclease map of the human BCDF Chromosomal gene as well as the organization of the four exons and the three introns are shown in FIG. 4, together with the strategy of the nucleotide sequencing analysis. The nucleotide sequence of the BamH/3.2 fragment which includes the actual human BCDF gene is shown in FIG. 5. The nucleotide sequence of the exon portions of the human BCDF chromosomal gene, thus clarified, completely coincided with the nucleotide sequence of human BCDF cDNA, which was revealed as described above.

It has been determined from the above results that the first exon in the chromosomal gene codes for the sequence between N-terminal first amino acid (Met) and the 48th amino acid (Glu) of the human BCDF precursor polypeptide, the second exon codes for the sequence between the 49th amino acid (Thr) and the 59th amino acid (Asn), the third exon codes for the sequence between the 60th amino acid (His) and the 102th amino acid (Lys), and the fourth exon codes for the sequence between the 103th amino acid (Lys) and the 134th amino acid (Ser).

(6) Construction of human BCDF expression vector

The following four expression vectors for animal cells were prepared from the human BCDF cDNA obtained in (2) above and the human BCDF chromosomal gene obtained in (5) above.

i) pdKCR-hIL-5cDNA ii) pdKCR-hIL-5cDNA-dhfr
iii) pdKCR-hIL-5gene
iv) pdKCR-hIL-5gene-dhfr

Figure 6:
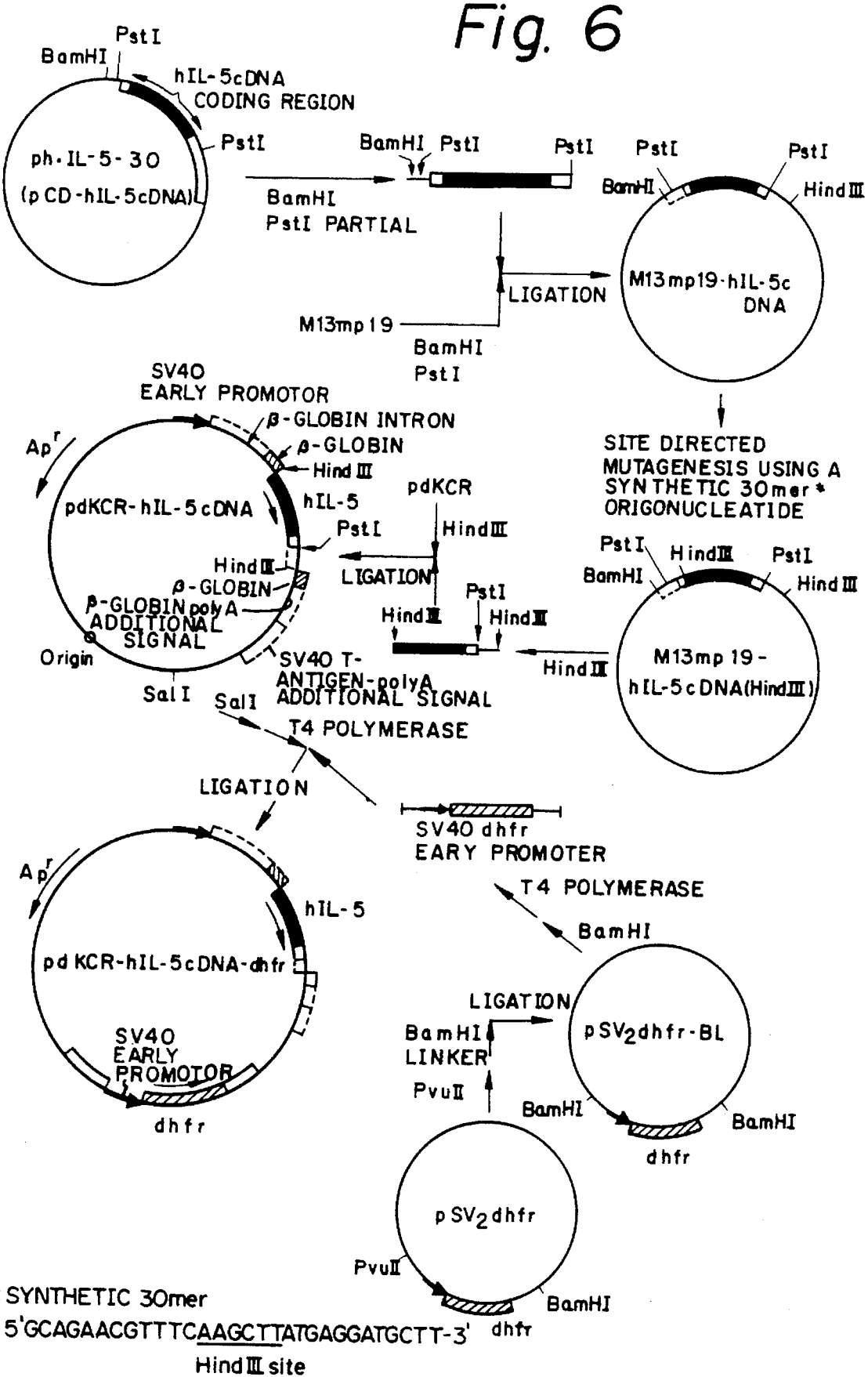
FIG. 6 shows the construction process of the cDNA expression vector pdKCR-hIL-5cDNA and pdKCR-hIL-5cDNA-dhfr.

A. Construction of pdKCR-hIL-5cDNA and pdKCR-hIL-5qDNA-dhfr FIG. 6 )

The clone of *E. coli* HB101 obtained in (2) above and named ph-IL-5-30 was used. The plasmid was isolated from this clone, subjected to BamHI digestion and PstI partial digestion, whereby a BamHI-PstI fragment was obtained. This fragment represents a cDNA containing the entire coding region of human BCDF. The subsequent cloning of said fragment between the BamHI and PstI sites of the phage M13mp19DNA resulted in M13mp19-hIL-5cDNA.

Subsequently, in order to introduce a HindIII site immediate 5' upstream to the human BCDF coding region, the site directed mutagenesis was conducted in accordance with the routine method [Messing, J. in Methods in Enzymology, vol. 101 Part C, pp 62–65 (Academic Press, Ed. Wu, R.)] using a 30-mer oligonucleotide:

5'-GCAGAACGTTTCAAGCTTATGAGGATGCTT-3' wherein the underlined AAGCTT represents the restriction sequence of HindIII, which hybridizes to the reverse sequence of the double underlined portion of the cDNA sequence of human BCDF as shown in FIG. 7, whereby a phage clone M13mp19-hIL-5cDNA (HindIII) was obtained. The DNA of this phage was digested with HindIII and the HindIII fragment containing a cDNA corresponding to the entire coding region of human BCDF was introduced in the right direction into the HindIII site of the vector pdKCR which vector was derived from pKCR vector by substituting a pBR327 site for the pBR322 site of the latter [Nikaido, T., et al., Nature, 311', 631–635 (1984)]. Thus, the expression vector pdKCR-hIL-5cDNA was obtained.

Next, the plasmid vector pdKCR-hIL-5cDNA was digested with SalI and the broken site was changed to a cohesive end by use of a T4 DNA polymerase so that the dihydrofolate reductase (dhfr) gene expressing unit would be introduced at the SalI site of said pdKCR-hIL-5cDNA vector. In order to prepare the fragment of the dhfr gene expressing unit employed here, a BamHI linker was added at the PvuII site of pSV$_2$hfr (BRL Inc.) to form the plasmid pSV$_2$dhfr-BL which was then digested with BamHI and the broken site was changed to a cohesive end by use of a T4 DNA polymerase, whereby the dhfr gene expression unit fragment was separated. The fragment was ligated to pdKCR-hIL-5cDNA having one cut as prepared above. The expression vector pdKCR-hIL-5cDNA-dhfr was thus obtained.

Figure 8:
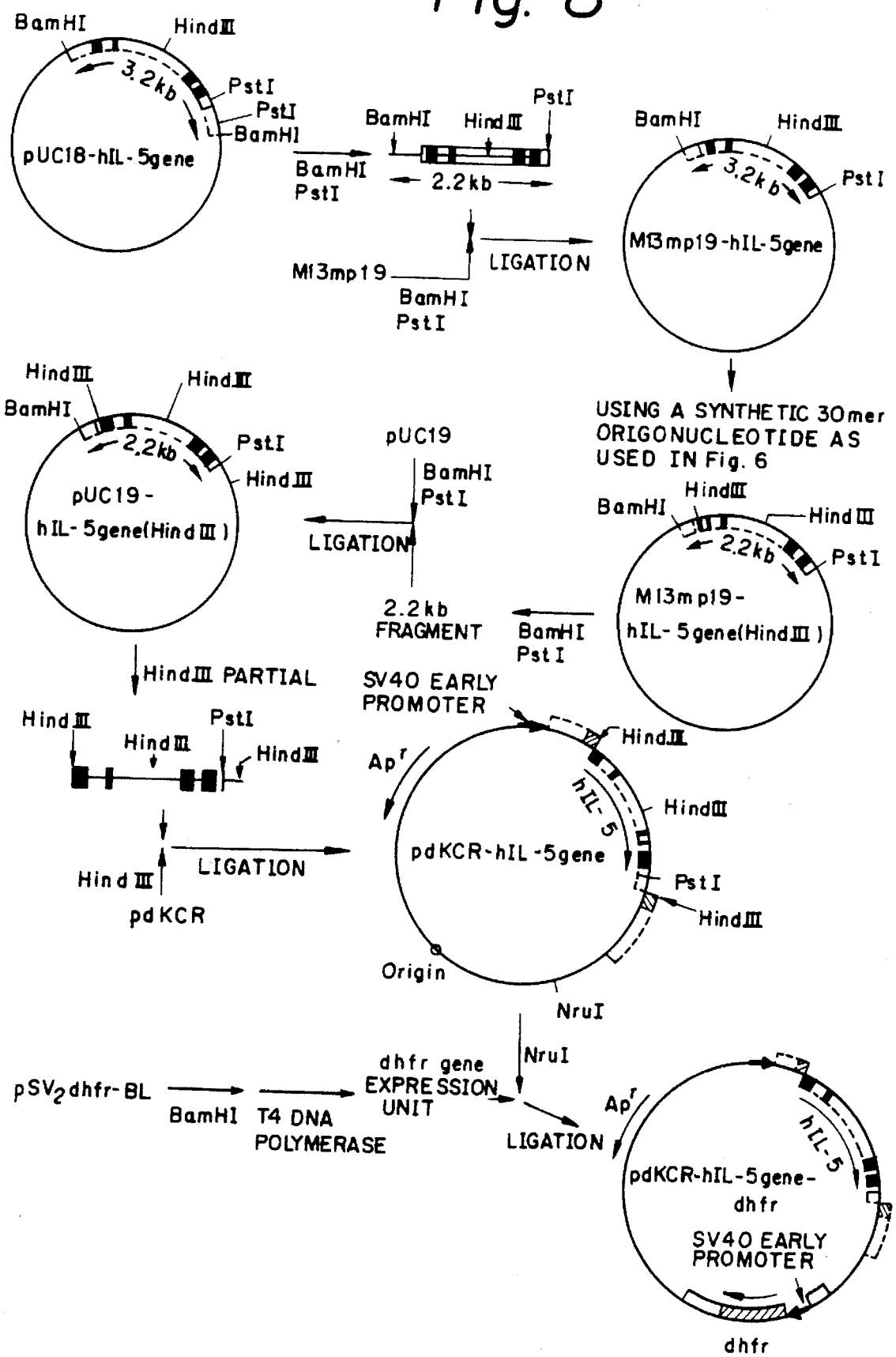
FIG. 8 shows the construction process of human BCDF expression vector pdKCR-hIL-5gene and pdKCR-hIL-5gene-dhfr.

B. Construction of pdKCR-hIL-5gene and pdKCR-hIL-5gene-dhfr (FIG. 8)

A 3.2 kb BamHI fragment containing the entire nucleotide sequence of human BCDF gene was separated from the phage clone λ12, which had been obtained in (5) above; said phage clone containing a human BCDF gene. The separated fragment was subcloned into the vector pUC18 to obtain a transformant pUC18-hIL-5gene. The plasmid of this transformant was digested with BamHI and PstI to obtain a 2.2 kb BamHI-PstI fragment containing the entire nucleotide sequence encoding human BCDF. The fragment was cloned between the BamHI and PstI sites of the phage M13mp19 DNA to obtain M13mp19-hIL-5gene. The site directed mutagenesis was subsequently carried out as described in A. above to obtain the clone M13mp19-hIL-5gene (HindIII) which has a HindIII site introduced at the immediate 5' upstream of the human BCDF coding region. The phage DNA so obtained was digested with BamHI and PstI, the separated human BCDF gene was subcloned into pUC19 and the so obtained plasmid pUC19-hIL-5gene (HindIII) was further digested partially with HindIII. The entire nucleotide region coding for human BCDF thus separated was introduced into the HindIII site of the vector pdKCR in the right direction to obtain the expression vector pdKCR-hIL-5gene. This plasmid pdKCR-hIL-5gene was digested with NruI for the purpose of introducing the dhfr gene expression unit at the NruI site of said expression vector and the dhfr gene expression unit obtained in A. above was ligated to the resulting cohesive end to obtain pdKCR-hIL-5gene-dhfr.

The four expression vectors thus prepared contained SV 40 (Simian virus 40) early promotor which governed the expression of human BCDF and dhfr together with the replication origin of SV 40. In addition the 5' and 3' nontranslated regions which are not required for the expression of the human BCDF cDNA or human BCDF chromosomal DNA were deleted from these expression vectors so that the expression of human BCDF would be increased.

(7) Expression of human BCDF in animal cells

The expression of human BCDF in COS-I or CHO cells were conducted by using the expression vectors prepared in the foregoing section (6).

The animal cell line COS-I (monkey kidney) was passaged in the Dulbecco's modified essential medium containing 10% fetal bovine serum. The transfection was conducted when the cells reached 50 to 70% confluent by the calcium phosphate method in accordance with the method of Graham, F. L. and van der Eb, A. J., Virology, 52, 456–467 (1973). The respective expression vector prepared in section (6) was used at 10 μg per cells in a culture dish of 10 cm (φ). The culture was continued for 3 days at 87° C., under 5% $CO_2$ while monitoring the supernatant for its BCDF activity. At the same time, the RNA of the cells was extracted using the method of Freeman et al. [Proc. Natl. Acad. Sci. USA, 80, 4094 (1983)]. The extracted RNA was subjected to the Northern blot analysis in accordance with the method of Nambu, J. R. et al. [Cell, 35, 47–56 (1983)] using the RNA at 20 μg/lane in order to determine the expression level of the human BCDF mRNA. The probe used for this analysis was a HindIII-PstI fragment of M13mp19-hIL-5cDNA (HindIII) containing the entire coding region of human BCDF.

The expression in CHO (chinese hamster ovary) was conducted in the strain CHOdhfr⁻. The cells were passaged in MEMα⁺ (GIBCO) containing 10% fetal bovine serum as the medium. The transfection was conducted as explained above. The expression vector was pdKCR-hIL-5cDNA-dhfr and pdKCR-hIL-5gene-dhfr. The cultivation was continued for further 48 hours after the transfection and then the cells were selected in MEMα⁻ (GIBCO) containing 10% dialyzed fetal bovine serum in accordance with the method of Weissman, C. [Nucleic Acids Res. 11, 687 (1983)]. Thereafter, 0.1 μM of methotrexate was added to the culture medium, the cultivation was continued for a further several days to isolate cell colonies which were resistant to methotrexate, the isolated colonies were passaged and the activity of BCDF in the culture supernatant was measured. In order to obtain a cell strain capable of expressing high level of human BCDF, methotrexate was added to the culture medium of the passaged cells at the concentrations which were gradually increased up to 1 mM in accordance with Simonsen, C. C. and Levinson, A. D. [Proc. Natl. Acad. Sci. USA, 80, 2495–2499 (1983)]. In this way a cell line which produces human BCDF was established.

The assay of human BCDF used was the measurement of the T cell replacing factor of Kinashi, T., et al. [Nature, 324, 70–73 (1986)]. The cells used in the assay was $BCL_1$ mouse chronic B leukemia cells [a strain passaged in vivo or the clone $5B_1b$ (ATCC TIB 197)], which were mixed with a series of successive dilution of the sample, seeded at $5\times10^3$ cells/200 µl among the wells of flat bottomed 96 well plates and they were cultivated for 48 hours under 5% $CO_2$, at 37° C. The culture medium comprised of RPMI-1640 containing 10% fetal bovine serum in addition to 2-mercaptoethanol, $5\times10^{-5}$ M, penicillin G, 50 U/ml and streptomycin, 50 µg/ml. The cells were collected 48 hours later by centrifugation, washed with Hank's solution, suspended using 200 µl/well of Hank's solution, and 100 µl of the cell suspension was used to conduct the protein A plaque assay in accordance with Gronowicz, E., et al. (Eur. J. Immonol., 6, 588–590 (1976)] to measure the number of IgM producing cells. Human BCDF could be detected conveniently in this assay system although sensitivity of the assay with respect to human BCDF was lower than mouse BCDF by an order of 1:100 when compared with purified BCDF samples since $BCL_1$ cells used originated from a mouse.

COS-I cells were transfected with the expression vectors pdKCR-hIL-5cDNA and pdKCR-hIL-5gene respectively, and the expression of human BCDF mRNA of the two transfectants was analyzed 3 days after using the Northern blot analysis which showed a hybridization band for both vectors at the size corresponding to 1 kb. The results indicated that the transcription product from the human BCDF gene is correctly spliced in COS-I cells. It was interestingly noted that the expression level of human BCDF mRNA by COS-I/pdKCR-hIL-5gene was about 20 times higher than by COS-I/pdKCR-hIL-5cDNA. The same tendency was also observed by the protein A plaque assay wherein the plaque forming colong number (PFC No.) of $BCL_1$ cells by the culture supernatant of COS-I cells transfected by these plasmids represented BCDF activity. Namely, the transfected COS-I cells were cultivated for 3 days, the culture supernatant was added at 20% to the culture of $BCL_1$ cells and the plaque formation of the cells was compared. As shown in Table 1 below, the PFC No. resulated from the plasmid pdKCR-hIL-5gene was 17 times higher than that from the plasmid pdKCR-hIL-5cDNA when these numbers were compared by the difference from the control (non-transfected host cell COS-I).

TABLE 1

Comparison of BCDF activity between the transfectants

| Transfectant | PFC No. | difference from the control |
|---|---|---|
| COS-I (Control) | 353 | (0) |
| COS-I/pdKCR-hIL-5cDNA | 393 | 30 |
| COS-I/pdKCR-hIL-5gene | 863 | 500 |

This higher expression was elucidated by a possible existence, in the introns of human BCDF gene, of an unknown enhancing mechanism capable of influencing on SV 40 promotor rather than by a possibility that the transfection efficiency of pdKCR-hIL-5gene is higher than that of pdKCR-hIL-5cDNA, although the latter possibility cannot be denied completely. The results of the Northern blot analysis agreed with the results of the bioassay using $BCL_1$ cells.

(8) Purification and characterization of human BCDF

COS-I cells were transfected by pdKCR-hIL-5gene, cultured for 3 days and human BCDF was purified from 640 ml of the 3 days-culture medium collected from 64 culture dishes of 10 cm (φ). After centrifugation, the supernatant was introduced and adsorbed on an affinity column (bed volume of 3 ml) containing Cellulofine (Chisso Co., Ltd., Japan) as the carrier on which rat anti-mouse-BCDF (IL-5) monoclonal antibody had been bound. This affinity column was employed for the purification because the conversion of $BCL_1$ cells into IgM producing cells by human BCDF was completely inhibited by the anti-mouse BCDF monoclonal antibody. The column was then washed in the following order.

i) 1M NaCl, 50 ml ii) 0.5% NP-40, 50 ml iii) PBS (pH 7.2), 50 ml iv) $H_2O$, 50 ml.

Figure 9:
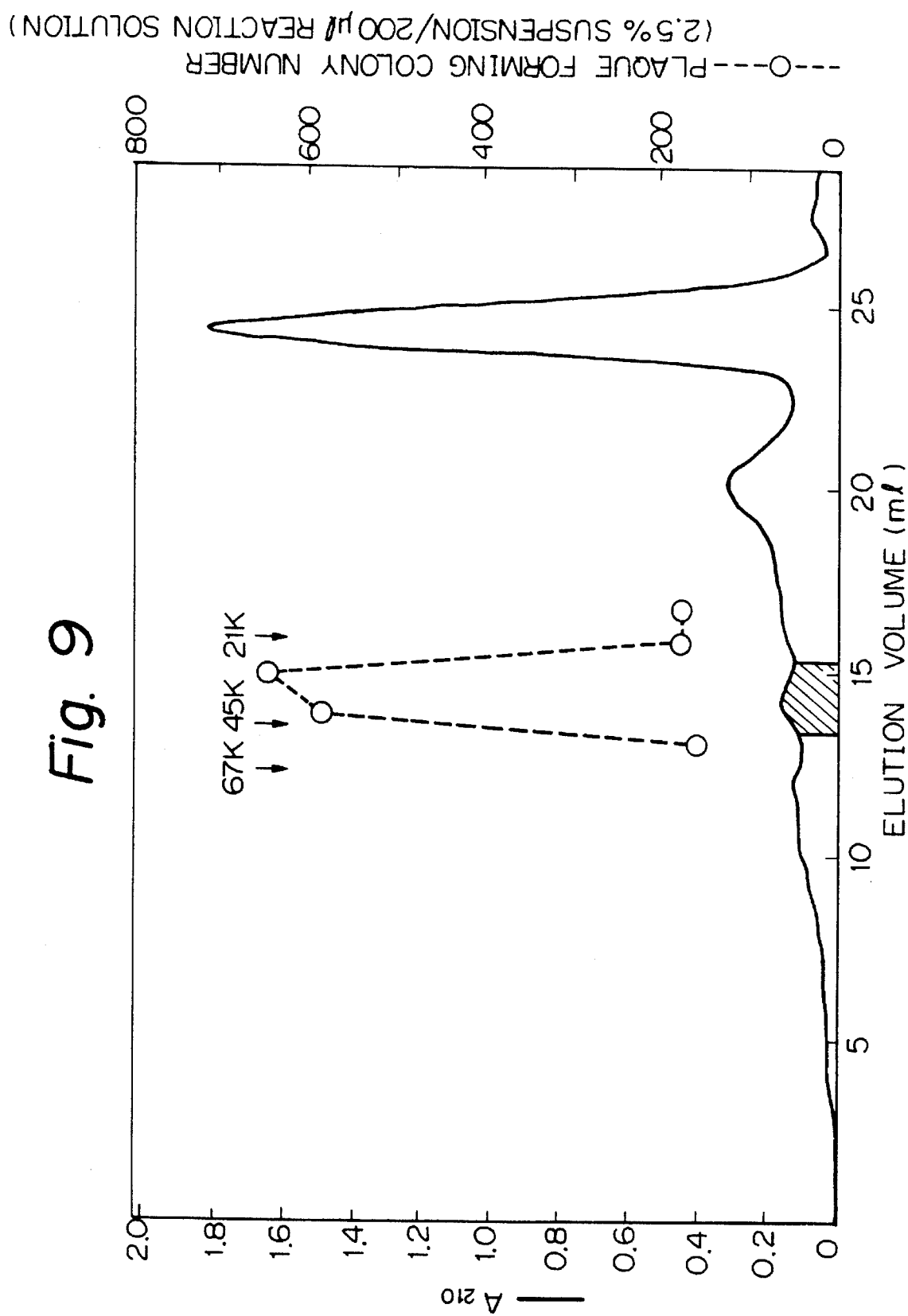
FIG. 9 shows the elution pattern of the recombinant human BCDF from the gel filtration column through a Superose 12 HPLC column.

Subsequently, the adsorbed human BCDF was eluted using 4 ml of 1M acetic acid and the eluted solution was concentrated upto 100 µl by use of a Speedbag concentrator. The concentrate was purified by HPLC using two columns of Superose 12 (Pharmacia Co.) which had been directly connected in line and had been equilibrated by PBS (pH 7.2). The elution from the column was conducted with the same buffered solution at the rate of 0.3 ml/min. The eluted solution was monitored with respect to $OD_{218}$ and the bioassay and the active fraction was collected at the approximate molecular weight of 40 K. The elution pattern is given in FIG. 9. The hatched portion in the figure represents the active fraction of BCDF, the solid line represents the elution pattern of the protein, the broken line represents the elution pattern of the BCDF activity, and the arrow indicate the elution positions of the standard molecular weight markers.

Figure 10:
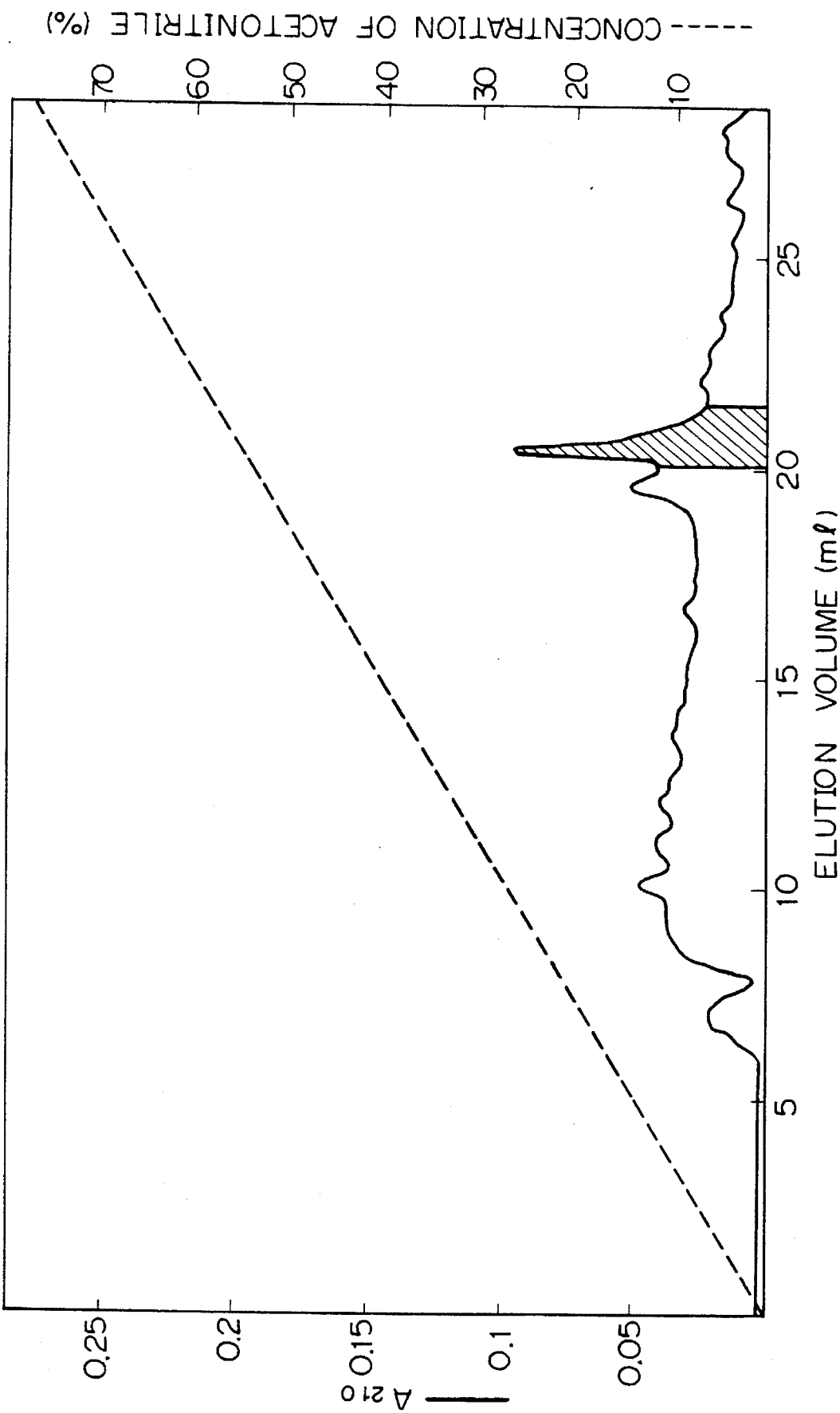
FIG. 10 shows the elution pattern of the recombinant human BCDF from the reverse phase HPLC on Senshu Pack VP-304-1251.

The active fraction was purified by a reverse phase HPLC on Senshu Pack VP-304-1251 (Senshu Kagaku Co., Ltd.) which corresponds to Protein $C_4$. The adsorbed human BCDF was eluted by the linear gradient of acetonitrile (0 to 80%) in 0.1% of trifluoroacetic acid (TFA) flowing at the rate of 0.5 ml/min. The elution pattern is shown in FIG. 10. The hatched portion in the figure represents the active fraction of BCDF and the broken line represents the concentration of acetonitrile. The purified human BCDF was collected at the elution point of approximately 55% acetonitrile. Thus the purified human BCDF yield was about 3 µg.

The measurement of the molecular weight of the purified human BCDF was conducted by a SDS-polyacrylamide gel electrophoresis using the sample at 0.15 µg/50 µl/lane. The results of the electrophoresis are shown in FIG. 11. The standard markers were run on lane 4) in the figure, and lanes 1) to 3) contained human BCDF after respective treatment under the following conditions.

Lane 1): the sample immediately after the purification; no treatment by 2-mercaptoethanol; no heat treatment;

Lane 2): the sample immediately after the purification; treated by 2-mercaptoethanol; no heat treatment;

Lane 3): the purified sample which had been preserved for 2 weeks in the eluting solution at 4° C.; no treatment by 2-mercaptoethanol; no heat treatment.

FIG. 11 shows that the human BCDF sample which had no experience of the 2-mercaptoethanol or the heat treatment showed a single band at about 40 K which coincides with the value in the gel filtration, whereas the sample experienced with the 2-mercaptoethanol treatment but with no heat treatment showed a single band on the gel at the molecular weight of about 20 K. Also, the sample formed a single band showing the molecular weight of about 20 K after being preserved in the eluting solution (0.1% TFA, ca. 55% acetonitrile) for 2 weeks at 4° C. even if the condition of said solution was oxidative. These facts suggest that the native form of human BCDF is a dimeric substance with a molecular weight of about 40 K each monomer being about 20 K.

The purified human BCDF 2 μg (about 100 pmole as a monomer) was used to determine the N-terminal amino acid sequence in accordance with the method of Hewick, R. M., et al. [J. Biol. Chem., 356, 7990–7997 (1981)] using a gas-phase protein sequencer. The phenylthio hydantoine amino acid (PTH amino acid) from each cycle was analyzed by the reverse phase HPLC and the first 27 amino acid sequence of the N-terminal was determined. The results are given in Table 2.

TABLE 2

| cycle | amino acid | PTH-amino acid recovered (pmole) |
|---|---|---|
| 1 | Ile | 12.0 |
| 2 | Pro | 8.3 |
| 3 | – | – |
| 4 | Glu | 5.6 |
| 5 | Ile | 6.9 |
| 6 | Pro | 5.7 |
| 7 | Thr | 1.6 |
| 8 | Ser | 1.8 |
| 9 | Ala | 3.2 |
| 10 | Leu | 2.5 |
| 11 | Val | 2.3 |
| 12 | Lys | 1.1 |
| 13 | Glu | 1.7 |
| 14 | Thr | 1.0 |
| 15 | Leu | 1.2 |
| 16 | Ala | 1.8 |
| 17 | Leu | 0.8 |
| 18 | Leu | 1.2 |
| 19 | Ser | 1.2 |
| 20 | Thr | + |
| 21 | – | – |
| 22 | – | – |
| 23 | – | – |
| 24 | Leu | 0.6 |
| 25 | Leu | 0.9 |
| 26 | Ile | 0.5 |
| 27 | Ala | 0.5 |

– not detected
+ detected but could not be quantified

The results indicated that the precursor of human BCDF comprising 134 amino acids, as deduced from the nucleotide sequence of human BCDF cDNA as determined in the foregoing section (3), undergoes a separation of the leader sequence by a breaking off of the 19th amino acid (Ala) at the C-terminal (see FIG. 3) when the human BCDF is secreted from animal cells, so that when it is secreted from COS-I cells or their possible natural source (T-cells) the secreted form is a sugar containing dimeric protein comprising a 115 amino acid sequence as its monomer component.

In said amino acid analysis, the third amino acid, which was deduced to be threonine from the nucleotide sequence, of the purified human BCDF was not detected even though the 7th, 14th and 20th threonine were detected. This fact strongly suggested that said third amino acid has a sugar chain which is attached thereto. This sugar chain was thought to be attached through an O-glycoside bonding.

The speculated two dimensional arrangement to the amino acid sequence of the human BCDF monomer is given in FIG. 12. The properties of the mature recombinant human BCDF expressed by COS-I cells are summarized as follows.

i) The peptide portion of human BCDF peptide comprises a homodimer. This is inferred from the facts that only one N-terminal amino acid sequence starting from isoleucine was detected, the molecular weight of human BCDF is about 40 K in the natural form and a band of about 20 K was detected on the SDS-polyacrylamide gel electrophoresis, when the BCDF sample was subjected to the treatment with 2-mercaptoethanol or to the long term treatment with 0.1% TFA—55% acetonitrile.

ii) The peptide portion of the monomer of mature human BCDF comprises 115 amino acids starting from isoleucine and the peptide portion of the monomer has a molecular weight 13,149.

iii) Mature human BCDF is a sugar containing dimeric polypeptide. This was inferred from the facts that the 28th and 71st asparagines in the mature human BCDF amino acid sequence provide positions capable of being N-glycosylated, the 3rd threonine seemed to be O-glycosylated since it could not be detected in the amino acid sequencing analysis, and the molecular weight of the monomer determined at about 20 K by the SDS-polyacrylamide gel electrophoresis was considerably different from the calculated value (13,149) based on its peptide sequence. Therefore, mature human BCDF monomer has, attached thereto, one or more sugar chains whose total molecular weight is about 7,000 or less.

iv) The state of the two cysteines at the 44th and the 86th positions from the N-terminal amino acid sequence of mature human BCDF have not been determined yet. However, the dimer did not seem to be formed by a S—S cross linking between the monomer molecules, since the SDS polyacyrlamide gel electrophoresis of human BCDF showed a single band of the molecular weight corresponding to the monomer after a long term treatment with 0.1% TFA—55% acetonitrile although the condition of said treatment was oxidative. However, an S—S cross link possibly exists in the monomer molecule whereby preserving a conformation necessary to form the dimer since-the dimer readily dissolves, when treated with 2-mercaptoethanol, into monomers as evidenced on the SDS polyacrylamide gel electrophoresis. These observations suggested that the 44th and the 86th cysteines form an intra-molecular cross link.

v) From the exon-intron arrangement, revealed by the human BCDF nucleotide analysis, it has been determined that the sequence between the 1st amino acid (Ile) and the 29th amino acid (Glu) of mature human BCDF is coded for by the first exon, the sequence between the 30th amino acid (Thr) and the 40th amino acid (Ash) is coded for by the second exon, the sequence between the 41st amino acid (His) and the 83rd amino acid (Lys) is coded for by the third exon and the sequence between the 84th amino acid (Lys) and the 115th amino acid (Set) is coded for by the fourth exon.

vi) The purification of human BCDF gave a purified human BCDF in a yield of approximately 3 μg starting from 640 ml of the culture medium of COS-I cells subjected to the transient expression. Considering that the efficiency of the transformation of COS-I cells was about $10^{-3}$, the expression level of the cell strain CHO/pdKCR-hIL-5gene-dhfr indicated that said strain could be employed in the commercial production of human BCDF and could be applied to extensive uses, including that of the pharmaceutical area.

According to the present invention, the DNA sequence coding for a substance having human BCDF I activity as well as the polypeptide sequence of said substance has been revealed. The present invention therefore has provided the possibility of a large scale production of human BCDF by way of the recombinant DNA technology.

The recombinant human BCDF obtainable in accordance with the present invention can be administered to human subjects as a useful drug for ameliorating infectious diseases or immune deficiency disorders.

We claim:

1. A human B-cell differentiation factor having the following amino acid sequence of formula II:

```
                        1
                       ILE-
PRO-THR-GLU-ILE-PRO-THR-SER-ALA-LEU-VAL-
                       21
LYS-GLU-THR-LEU-ALA-LEU-LEU-SER-THR-HIS-

ARG-THR-LEU-LEU-ILE-ALA-ASN-GLU-THR-LEU-
                       41
ARG-ILE-PRO-VAL-PRO-VAL-HIS-LYS-ASN-HIS-

GLN-LEU-CYS-THR-GLU-GLU-ILE-PHE-GLN-GLY-
                       61
ILE-GLY-THR-LEU-GLU-SER-GLN-THR-VAL-GLN-

GLY-GLY-THR-VAL-GLU-ARG-LEU-PHE-LYS-ASN-
                       81
LEU-SER-LEU-ILE-LYS-LYS-TYR-ILE-ASP-GLY-

GLN-LYS-LYS-LYS-CYS-GLY-GLU-GLU-ARG-ARG-
                      101
ARG-VAL-ASN-GLN-PHE-LEU-ASP-TYR-LEU-GLN-

GLU-PHE-LEU-GLY-VAL-MET-ASN-THR-GLU-TRP-
                      115
         ILE-ILE-GLU-SER
```

2. A human B-cell differentiation factor according to claim 1, which has been produced by recombinant technology and has been purified to such an extent that it will be eluted as a single component from a high performance liquid chromatography column, using the Protein $C_4$ type adsorbent, and that it will be detected as a single band on the SDS polyacrylamide gel electrophoresis.

3. A human B-cell differentiation factor according to claim 1, which is a sugar containing protein comprising a monomer or dimer of a component whose polypeptide portion has an approximate molecular weight of 13,149 Daltons.

4. A human B-cell differentiation factor according to claim 1 wherein at least the third amino acid residue (Thr) of the N-terminal has a sugar chain attached thereto.

5. A human B-cell differentiation factor according to claim 3 wherein said monomer forms a dimer having an approximate molecular weight of 40,000 Daltons.

6. A precursor polypeptide of a human B-cell differentiation factor according to claim 1, which has the following amino acid sequence of formula:

```
Met Arg Met Leu Leu His Leu Ser Leu Leu
Ala Leu Gly Ala Ala Tyr Val Tyr Ala Ile
Pro Thr Glu Ile Pro Thr Ser Ala Leu Val
Lys Glu Thr Leu Ala Leu Leu Ser Thr His
Arg Thr Leu Leu Ile Ala Asn Glu Thr Leu
Arg Ile Pro Val Pro Val His Lys Asn His
Gln Leu Cys Thr Glu Glu Ile Phe Gln Gly
Ile Gly The Leu Glu Ser Gln Thr Val Gln
Gly Gly Thr Val Glu Arg Leu Phe Lys Asn
Leu Ser Leu Ile Lys Lys Tyr Ile Asp Gly
Gln Lys Lys Lys Cys Gly Glu Glu Arg Arg
Arg Val Asn Gln Phe Leu Asp Tyr Leu Gln
Glu Phe Leu Gly Val Met Asn Thr Glu Trp
Ile Ile Glu Ser
```

* * * * *